United States Patent
Alexeenko et al.

(10) Patent No.: US 10,161,818 B2
(45) Date of Patent: Dec. 25, 2018

(54) MICROELECTROMECHANICAL GAS SENSOR BASED ON KNUDSEN THERMAL FORCE

(71) Applicant: Purdue Research Foundation, West Lafayette, IN (US)

(72) Inventors: Alina Alexeenko, West Lafayette, IN (US); Andrew Strongrich, Saginaw, MI (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 108 days.

(21) Appl. No.: 15/183,259

(22) Filed: Jun. 15, 2016

(65) Prior Publication Data

US 2016/0363553 A1    Dec. 15, 2016

Related U.S. Application Data

(60) Provisional application No. 62/180,047, filed on Jun. 15, 2015.

(51) Int. Cl.
| | |
|---|---|
| *G01N 7/00* | (2006.01) |
| *G01N 9/00* | (2006.01) |
| *G01L 9/00* | (2006.01) |
| *G01N 27/22* | (2006.01) |

(52) U.S. Cl.
CPC .............. *G01L 9/00* (2013.01); *G01N 27/226* (2013.01)

(58) Field of Classification Search
CPC ............ G01L 21/26; G01L 9/00; G01N 27/22
USPC ......................................... 73/31.05
See application file for complete search history.

(56) References Cited

U.S. PATENT DOCUMENTS 6,127,765 A * 10/2000 Fushinobu .......... B81C 1/00968
                                                        216/52

OTHER PUBLICATIONS

Authors:Shanmukha Vikrant Sista and Enakshi Bhattacharya, Title: Knudsen force based MEMS structures, Date: Mar. 10, 2014, Publisher: IOP Publishing, Journal of Micromechanics and Microengineering, vol. 24, pp. 6.*

* cited by examiner

*Primary Examiner* — Lisa Caputo
*Assistant Examiner* — Roger Hernandez-Prewit
(74) *Attorney, Agent, or Firm* — Purdue Research Foundation (57) ABSTRACT

A system operating based on Knudsen thermal force includes a microelectromechanical (MEMS) gas sensor, the MEMS gas sensor includes a substrate. The sensor further includes at least one stationary assembly fixedly coupled to the substrate, the at least one stationary assembly terminating at corresponding pads configured to receive an electrical current for heating the at least one stationary assembly. Additionally, the sensor includes at least one moveable assembly disposed above the substrate and biased to move substantially according to a main axis and juxtaposed with the at least one stationary assembly.

8 Claims, 6 Drawing Sheets

MICROELECTROMECHANICAL GAS SENSOR BASED ON KNUDSEN THERMAL FORCE

CROSS-REFERENCE TO RELATED APPLICATIONS

The present U.S. patent application is related to and claims the priority benefit of U.S. Provisional Patent Application Ser. No. 62/180,047, filed Jun. 15, 2015, the contents of which is hereby incorporated by reference in its entirety into the present disclosure.

GOVERNMENT SUPPORT CLAUSE

This invention was made with government support under 1055453 awarded by the National Science Foundation. The government has certain rights in the invention.

TECHNICAL FIELD

The present application relates to microelectromechanical (MEMS) sensors, and specifically to microelectromechanical gas sensors operating based on Knudsen thermal force.

BACKGROUND

This section introduces aspects that may help facilitate a better understanding of the disclosure. Accordingly, these statements are to be read in this light and are not to be understood as admissions about what is or is not prior art.

There are several technologies that are utilized to measure pressure. For example, mono-crystalline or polycrystalline silicon are used in piezoresistive pressure sensor. Typically, the mean-free path dictates a length much smaller than the typical micro-scale dimensions. However, at lower pressures, the mean-free paths are larger and are in the order of the typical micro-scale dimensions.

There is an unmet need for a novel MEMS based pressure sensor system that can operate at low pressures.

SUMMARY

A microelectromechanical (MEMS) gas sensor operating based on Knudsen thermal force is disclosed. The sensor includes a substrate. The sensor also includes at least one stationary assembly that is fixedly coupled to the substrate, the at least one stationary assembly terminating at corresponding pads configured to receive an electrical current for heating the at least one stationary assembly. The sensor further includes at least one moveable assembly that is positioned above the substrate which is biased to move substantially according to a main axis and juxtaposed with the at least one stationary assembly. The at least one moveable assembly is configured to be selectively moveable along the main axis with respect to the at least one stationary assembly such that pressure applied to the at least one stationary assembly in the heated state and the at least one moveable assembly forms Knudsen forces applied to the at least one moveable assembly causing active movement of the at least one moveable assembly substantially along the main axis.

The at least one stationary assembly of the MEMS includes a base portion and at least one heating arm extended outward from the base portion.

The at least one moveable assembly of the MEMS includes a base portion, and at least one sensing arm extended from the base portion, the at least one extended sensing arm juxtaposed with a corresponding heating arm.

The MEMS further includes an actuation mechanism coupled to an actuation end of the at least one moveable assembly and configured to cause the selective movement, and a sensing mechanism coupled to a sensing end of the at least one moveable assembly opposite the actuation end, the sensing mechanism configured to sense the active movement of the at least one moveable assembly.

The at least one stationary assembly of the MEMS further includes one or more heating arms extended from the associated base portion, and the at least one moveable assembly further comprising one or more sensing arms extended from the associated base portion, each extended sensing arm juxtaposed with a corresponding heating arm.

The MEMS further includes one or more stationary assemblies each fixedly coupled to the substrate, and one or more moveable assemblies each disposed above the substrate and biased to move substantially according to the main axis and juxtaposed with an associated one or more stationary assemblies.

The actuation mechanism of MEMS includes an actuation capacitor coupled to actuation pads, such that applying a voltage to the actuation pads results in the selective movement of the moveable assembly due to electrostatic forces, and the sensing mechanism includes a sensing capacitor coupled to sensing pads, such that the active movement of the moveable assembly results in changes in capacitance of the sensing capacitor.

A microelectromechanical (MEMS) gas sensor operating based on Knudsen thermal force is disclosed. The sensor includes a substrate. The sensor further includes at least one stationary assembly fixedly coupled to the substrate, the at least one stationary assembly terminates at corresponding pads and is configured to receive an electrical current for heating the at least one stationary assembly. The at least one moveable assembly is positioned above the substrate and biased to move substantially according to a main axis and juxtaposed with the at least one stationary assembly. The at least one moveable assembly is configured to be selectively moveable with respect to the at least one stationary assembly such that at a known pressure applied to the at least one stationary assembly in the heated state and the at least one moveable assembly, movement of the at least one moveable assembly correlated to identity of concentration of known constituents of gases applying the known pressure.

The at least one stationary assembly of the MEMS includes a base portion and at least one heating arm extended outward from the base portion.

The at least one moveable assembly of the MEMS includes a base portion, and at least one sensing arm extended from the base portion, the at least one extended sensing arm juxtaposed with a corresponding heating arm.

The MEMS further includes an actuation mechanism coupled to an actuation end of the at least one moveable assembly and configured to cause the selective movement, and a sensing mechanism coupled to a sensing end of the at least one moveable assembly opposite the actuation end, the sensing mechanism configured to sense the active movement of the at least one moveable assembly.

The at least one stationary assembly of the MEMS further includes one or more heating arms extended from the associated base portion, and the at least one moveable assembly further comprising one or more sensing arms extended from the associated base portion, each extended sensing arm juxtaposed with a corresponding heating arm.

The MEMS further includes one or more stationary assemblies each fixedly coupled to the substrate, and one or more moveable assemblies each disposed above the substrate and biased to move substantially according to the main axis and juxtaposed with an associated one or more stationary assemblies.

The actuation mechanism of MEMS includes an actuation capacitor coupled to actuation pads, such that applying a voltage to the actuation pads results in the selective movement of the moveable assembly due to electrostatic forces, and the sensing mechanism includes a sensing capacitor coupled to sensing pads, such that the active movement of the moveable assembly results in changes in capacitance of the sensing capacitor.

A system operating based on Knudsen thermal force is disclosed. The system includes a microelectromechanical (MEMS) gas sensor. The MEMS includes a substrate. The MEMS also includes at least one stationary assembly that is fixedly coupled to the substrate, the at least one stationary assembly terminates at corresponding pads and configured to receive an electrical current for heating the at least one stationary assembly. The at least one moveable assembly is positioned above the substrate and is biased to move substantially according to a main axis and juxtaposed with the at least one stationary assembly. The at least one moveable assembly is configured to be selectively moveable along the main axis with respect to the at least one stationary assembly such that pressure applied to the at least one stationary assembly in the heated state and the at least one moveable assembly forms Knudsen forces applied to the at least one moveable assembly causing active movement of the at least one moveable assembly substantially along the main axis. The system further includes an actuation mechanism coupled to an actuation end of the at least one moveable assembly and configured to cause the selective movement. The system further includes a sensing mechanism coupled to a sensing end of the at least one moveable assembly opposite the actuation end, the sensing mechanism configured to sense the active movement of the at least one moveable assembly.

The at least one stationary assembly of the MEMS includes a base portion, and at least one heating arm extended outward from the base portion.

The at least one moveable assembly of the MEMS includes a base portion, and at least one sensing arm extended from the base portion, the at least one extended sensing arm juxtaposed with a corresponding heating arm.

The at least one stationary assembly of the MEMS further includes one or more heating arms extended from the associated base portion, and the at least one moveable assembly further comprising one or more sensing arms extended from the associated base portion, each extended sensing arm juxtaposed with a corresponding heating arm.

The MEMS further includes one or more stationary assemblies each fixedly coupled to the substrate, and one or more moveable assemblies each disposed above the substrate and biased to move substantially according to the main axis and juxtaposed with an associated one or more stationary assemblies.

The actuation mechanism includes an actuation capacitor coupled to actuation pads, such that applying a voltage to the actuation pads results in the selective movement of the moveable assembly due to electrostatic forces, and the sensing mechanism comprising a sensing capacitor coupled to sensing pads, such that the active movement of the moveable assembly results in changes in capacitance of the sensing capacitor.

BRIEF DESCRIPTION OF THE DRAWINGS

The above and other objects, features, and advantages of the present disclosure will become more apparent when taken in conjunction with the following description and drawings wherein identical reference numerals have been used, where possible, to designate identical features that are common to the figures, and wherein.

The attached drawings are for purposes of illustration and are not necessarily to scale.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

A novel microelectromechanical (MEMS)-based pressure sensor is disclosed herein that is capable of selectively providing a high sensitivity pressure reading as well as relative species concentration for a known ambient gases mixture.

Figure 1:
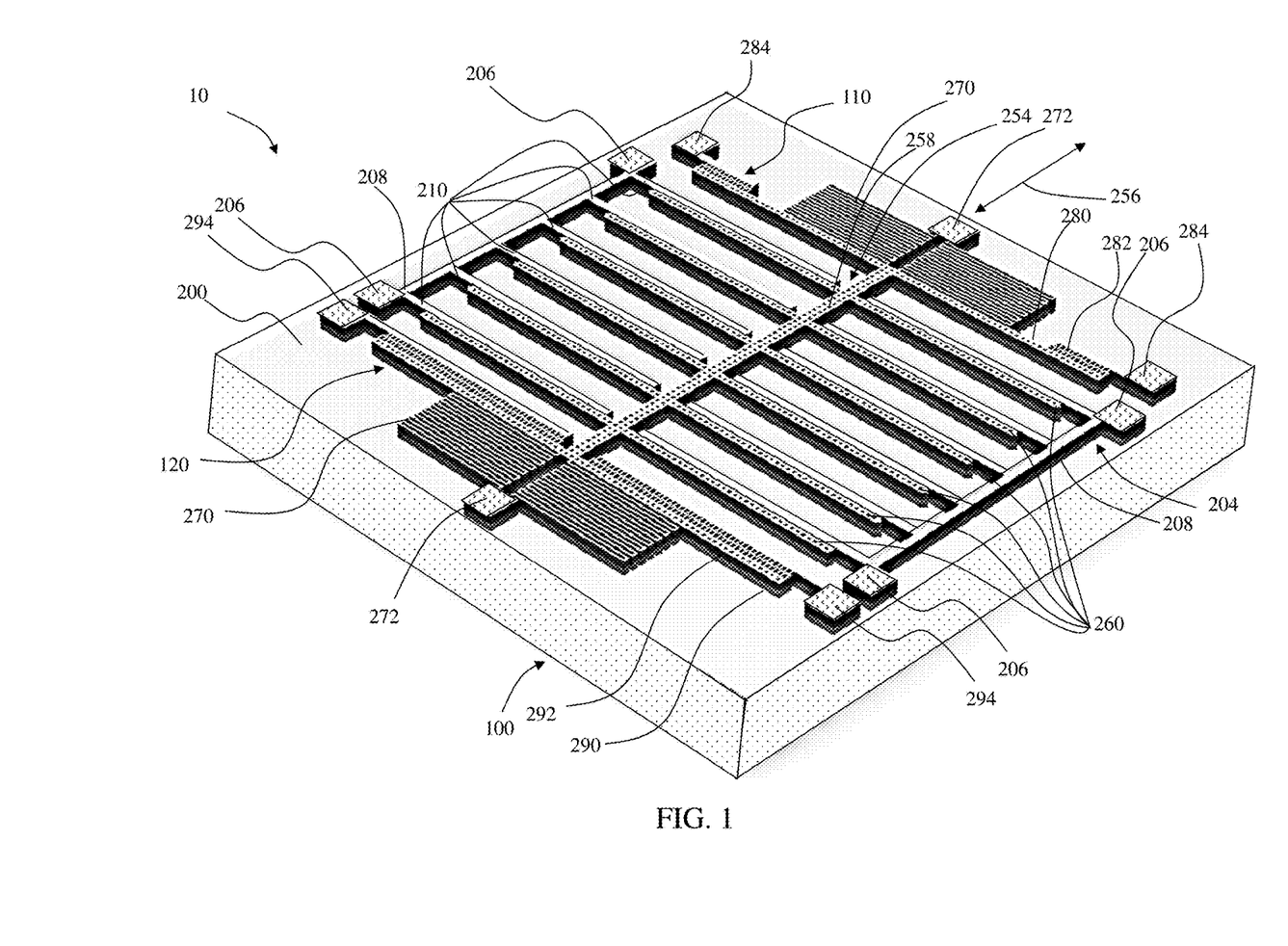
FIG. 1 depicts a perspective view of a system operating based on Knudsen thermal force, including a microelectromechanical (MEMS) gas sensor having a stationary assembly and a moveable assembly, an actuation mechanism, and a sensing mechanism.

Referring to FIG. 1, a non-limiting embodiment of a system 10 operating based on Knudsen thermal force according to the present disclosure is provided. The system 10 in general includes a microelectromechanical (MEMS) gas sensor 100, an actuation mechanism 110 and a sensing mechanism 120. The MEMS gas sensor 100 includes a substrate 200, e.g., silicon, and at least one stationary assembly 204 disposed above and fixedly coupled to the substrate 200. The stationary assembly 204 includes a base portion 208 terminating at corresponding pads 206 and at least one elongated heating arm 210, the heating arm 210 is heated corresponding to electrical current that passes through the pads 206. The MEMS gas sensor 100 further includes at least one moveable assembly 254 also disposed above the substrate 200 but configured to move substantially in the direction of a main axis 256. The moveable assembly 254 (also referred to as shuttle) is defined by an actuating end 280 and a sensing end 290. The moveable assembly 254 includes a base portion 258 and at least one sensing arm 260 extending from the base portion 258, each sensing arm 260 is juxtaposed with a corresponding elongated heating arm 210.

The MEMS gas sensor 100 of the system 10 also includes biasing members 270 coupled between the moveable assembly 254 and anchors 272. The anchors provide both electrical connectivity to ground as well as fixation to the substrate 200. In one embodiment, anchors 272 can be wire bond pads, known to a person having ordinary skill in the art. One biasing member 270 is connected to the moveable assembly 254 at the actuation end 280, while the other biasing member 270 is connected to the moveable assembly 254 at the sensing end. The anchors 272 are fixedly attached to the substrate 200 thereby causing one side of the biasing members 270 to be fixedly attached to the substrate 200. In this arrangement, the moveable assembly, the biasing members 270, and the anchors 272 all are at ground level, electrically.

Also as discussed above, the system 10 with the MEMS gas sensor 100 also includes an actuating mechanism 110 configured to selectively move the moveable assembly 254 in plane with respect to the stationary assembly 204 substantially along the main axis 256. According to one embodiment, the actuating mechanism 110 is configured to move the moveable assembly 254 based on measured resistance of the heating elements corresponding to a temperature and output from the sensing mechanism 120. The resistance measurement can be correlated to heat exchange with the ambient gas, thereby providing a correlation to the concentration of known constituents of the ambient gas.

The actuating mechanism 110 includes at least one actuation capacitor 282 coupled to actuation pads 284 on one side of the actuation capacitor 282 while coupled to the moveable assembly 254 on the other side of the actuation capacitor 282. In FIG. 1, two actuation capacitors 282 are shown. The actuation capacitors 282 are formed as combs, e.g., providing between 40 and 60 capacitors (nominally about 52 capacitors). Applying a voltage to the actuation pads 284 places charge in the actuation capacitors 282 causing a repelling force between the plates of the actuation capacitors 284, which causes selective movement of the moveable assembly 254.

As discussed above, the system 10 with the MEMS gas sensor 100 also includes a sensing mechanism 120 configured to measure movement of the moveable assembly 254 with respect to the stationary assembly 204. The output of the sensing mechanism 120 corresponds to a pressure applied to the MEMS gas sensor 100.

The sensing mechanism 120 includes at least one sensing capacitor 292 (two are shown in FIG. 1) coupled to the moveable assembly 254 at the sensing end 290 and to the biasing member 270. The sensing capacitor 292 is electrically coupled to the sensing pads 294 which can be used to measure capacitance and which can be correlated to the movement of the moveable assembly 254 as a result of pressure applied to the MEMS gas sensor 100. The anchors provide both electrical connectivity to ground as well as fixation to the substrate 200. In one embodiment, anchors 272 can be wire bond pads, known to a person having ordinary skill in the art. As discussed above, one biasing member 270 is connected to the moveable assembly 254 at the actuation end 280, while the other biasing member 270 is connected to the moveable assembly 254 at the sensing end. The anchors 272 are fixedly attached to the substrate 200 thereby causing one side of the biasing members 270 to be fixedly attached to the substrate 200. In this arrangement, the moveable assembly, the biasing members 270, and the anchors 272 all are at ground level, electrically. In the embodiment shown in FIG. 1, the pair of sensing capacitors 292 are formed as combs providing between 150-200 capacitors (nominally about 188 capacitors) for the sensing mechanism 120.

Figure 2:
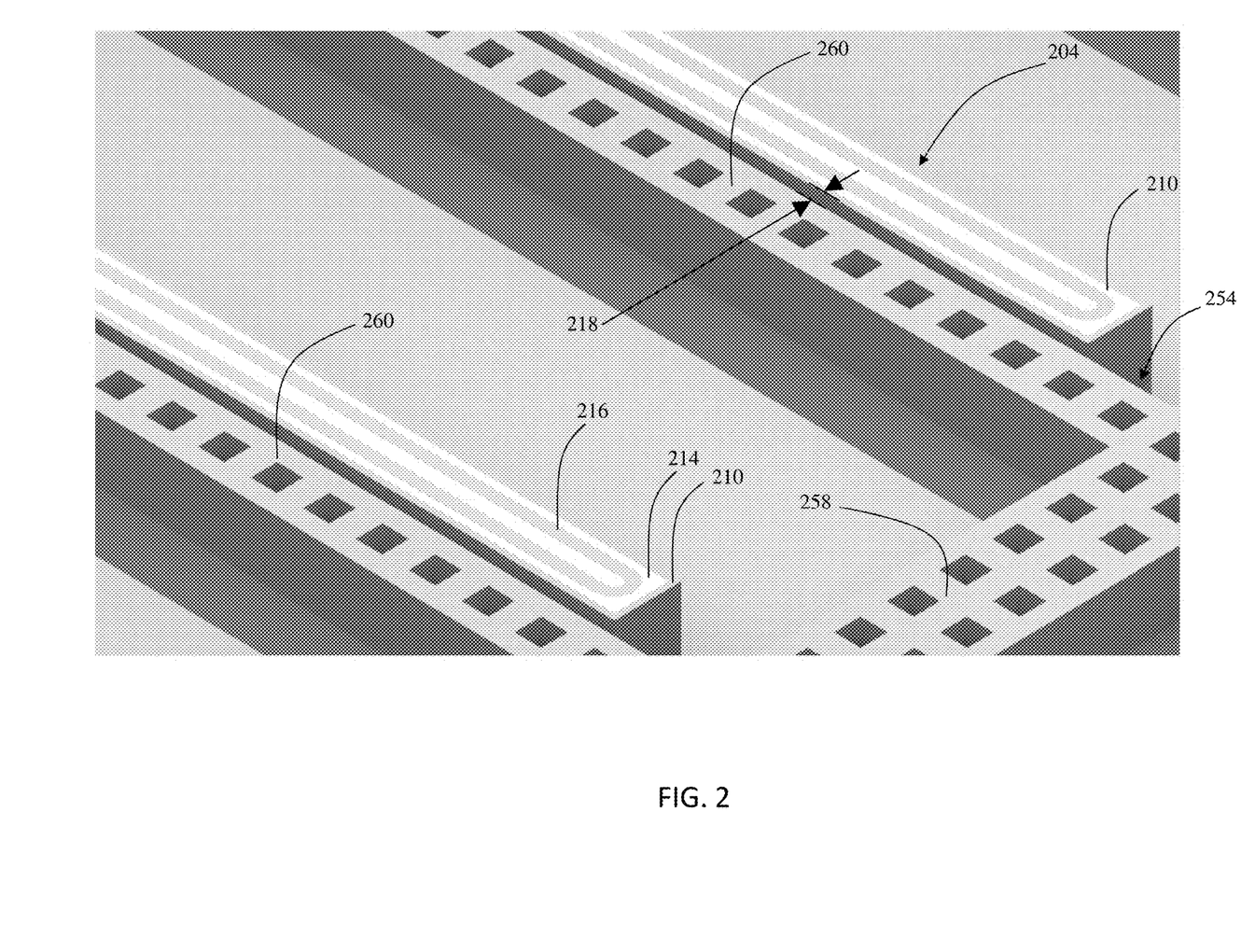
FIG. 2 depicts a close-up perspective view of the relationship between the stationary assembly and the moveable assembly of FIG. 1.
Figure 3A:
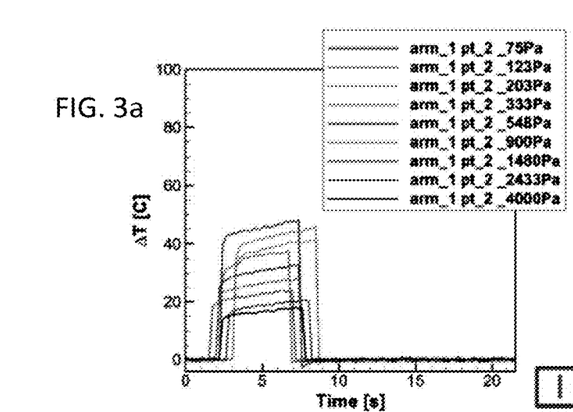
FIG. 3a-3d are plots of measured temperature gradients (in ° C.) vs. time (in s) for different pairs of heating arms of the stationary assembly and sensing arms of the moveable assembly of FIG. 1 at different pressures.
Figure 3B:
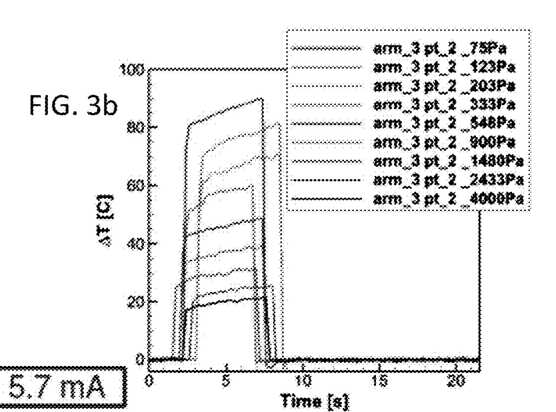
Figure 3C:
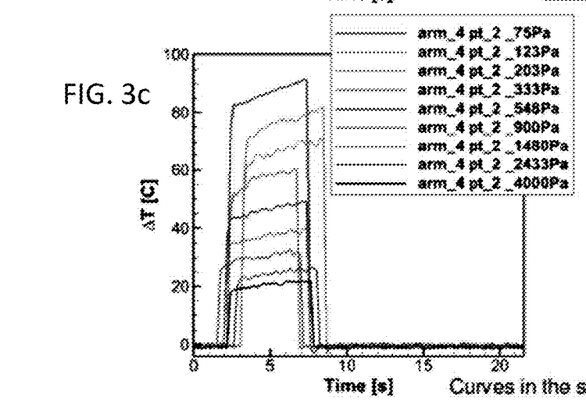
Figure 3D:
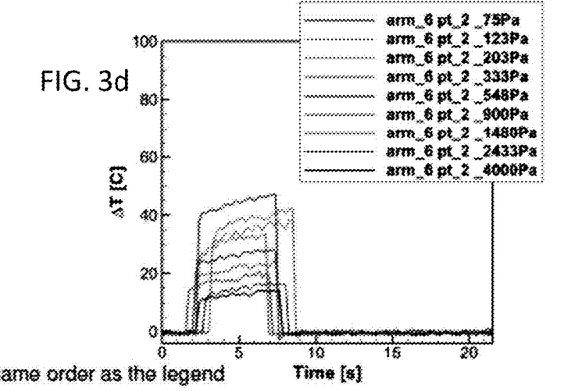

FIG. 2 depicts closer details of the MEMS gas sensor 100 embodiment shown in FIG. 1. Shown in FIG. 2 are the stationary assembly 204 and the moveable assembly 254, the base portion 258 of the moveable assembly 254, heating arms 210 of the stationary assembly 204, and sensing arms 260 of the moveable assembly 254. A gap 218 is called out between the heating arm 210 and sensing arm 260. This gap 218 changes as the moveable assembly moves, either selectively by charging actuation capacitors 282 or by application of Knudsen forces due to pressure applied to the MEMS gas sensor 100. The gap 218, therefore, represents an important characteristic that can be correlated to the pressure reading provided by the sensing mechanism 120 based on capacitance measurements of the sensing capacitor 292. Additionally and as described above, the gap 218 can be selectively adjusted by applying a voltage to the actuation pads 284 in order to i) maintain the highest sensitivity for the pressure measurement given the measured resistance (leading to temperature of the heating element or heat transfer rate), ii) dynamically tune to achieve the highest sensitivity to ambient conditions, and iii) calibrate for spring constant of the biasing members 270 and capacitance vs. displacement measurements. In one embodiment, the MEMS gas sensor 100 of the present disclosure uses a gap 128 of 5-100 μm (nominally about 20 μm) and suspended between 1-10 μm (nominally about 4 μm) above an underlying substrate 200.

As discussed above, the heating arms 210 are fixedly attached to the substrate 200, by e.g. thermal oxide, whereas the sensing arms are suspended by biasing members 270 allowing the moveable assembly 254 and its sensing arms 210 to displace away from the heating arms 210 under the action of Knudsen forces.

Shown n FIG. 2, are heating elements 216 (e.g., platinum between 5-15 μm, nominally about 10 μm) embedded in a thermally conducting but electrically isolating medium 214 (e.g., silicon nitride) provided to generate a thermal gradient between the heater arms 210 and surrounding gas and structures, e.g., the sensing arms 260.

For low ambient pressures (p<1 mTorr for a gap of 20 μm), the mean-free path of the gas molecules is larger than the gap separating the sensing arms 260 and the heating arms 210. An imbalance in momentum between the opposing heater and surfaces of the sensing arms 260 is generated and ultimately leads to a net repulsive force between the moveable assembly 254 and the stationary assembly 204. Using kinetic theory it can be shown that force magnitude increases linearly with pressure. As pressure is increased, the ballistic trajectories of the molecules are interrupted by intermolecular collisions allowing kinetic energy to be exchanged with other species before reaching the shuttle surface. Force production in this regime varies inversely with pressure and results from thermal stresses developed within the gas. The resultant displacement of the shuttle varies non-monotonically with pressure and thus can be sensed capacitively by the sensing mechanism 120 at the sensing end 290 to determine the pressure and concentration of known constituents of the gas applying pressure to the MEMS gas sensor 100.

Since both heat transfer rate and displacement are measured, it allows to extract both gas pressure and relative species concentration for a known ambient gases mixture.

The combined sensitivity to gas composition, pressure, and temperature gradient within this compact, all-electronic microsystem makes it attractive for pharmaceutical lyophilization, high-altitude UAV/spacecraft and other applications requiring sensing of gaseous environment, especially at low pressures.

Referring to FIG. 3a-3d, plots of temperature gradients (in ° C.) vs. time (in s) are shown for different pairs of heating arms 210 and sensing arms 260. The plots are provided for temperature measurements at approximately mid-point along the lengths of the heating arms 210 and sensing arms 260 for different ambient gas pressures. The plots show that peripheral arm pairs are at a lower temperature than central arm pairs.

Figure 4:
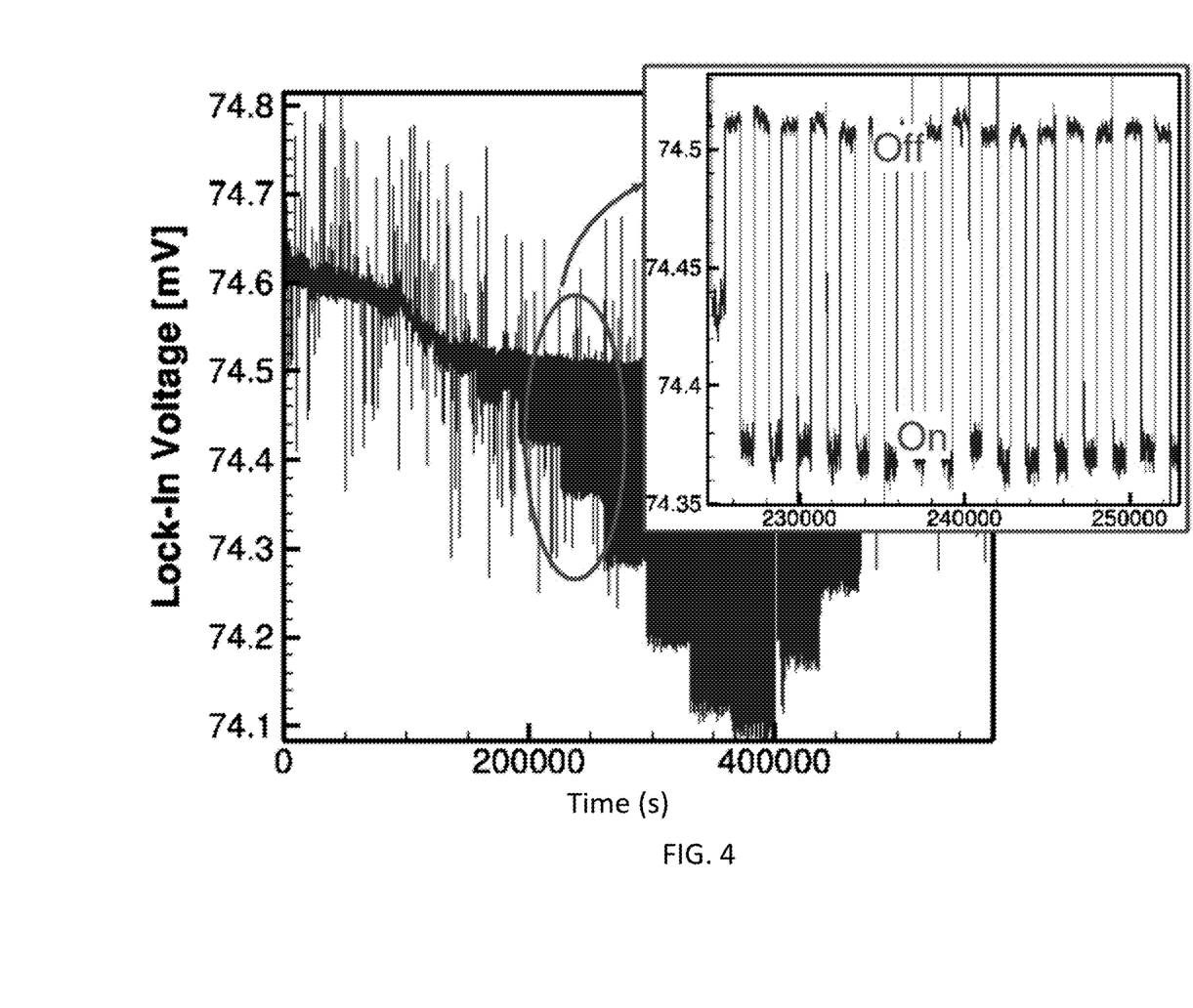
FIG. 4 is a plot of different lock-in voltages measured as a function of time as heating elements of the heating arms are cycled on and off.

Referring to FIG. 4, different lock-in voltages measured at the sensing pads 294 are provided as a function of time as the heating elements 216 of the heating arms 210 are cycled on and off. The variation in the plot is due to changes in the ambient pressure.

Figure 5:
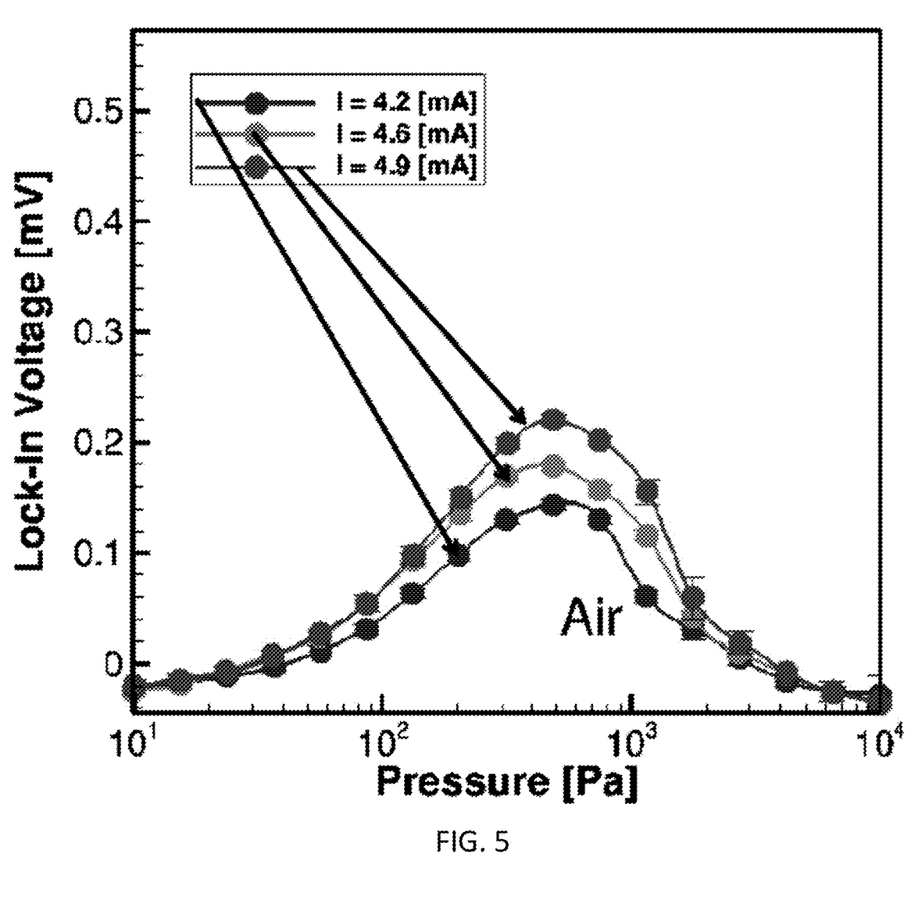
FIG. 5 provides plots of different lock-in voltages (in mV) measured at the sensing pads of the sensing mechanism of FIG. 1 as a function of time (in s) as the heating arms are activated and deactivated shown at different pressures.

Referring to FIG. 5, plots of pressure (in Pa) at different lock-in voltages (in mV) measure at the sensing pads 294 are provided. The plots indicate different lock-in voltages for air as the ambient gas at different current levels applied to the heating elements 216.

Figure 6:
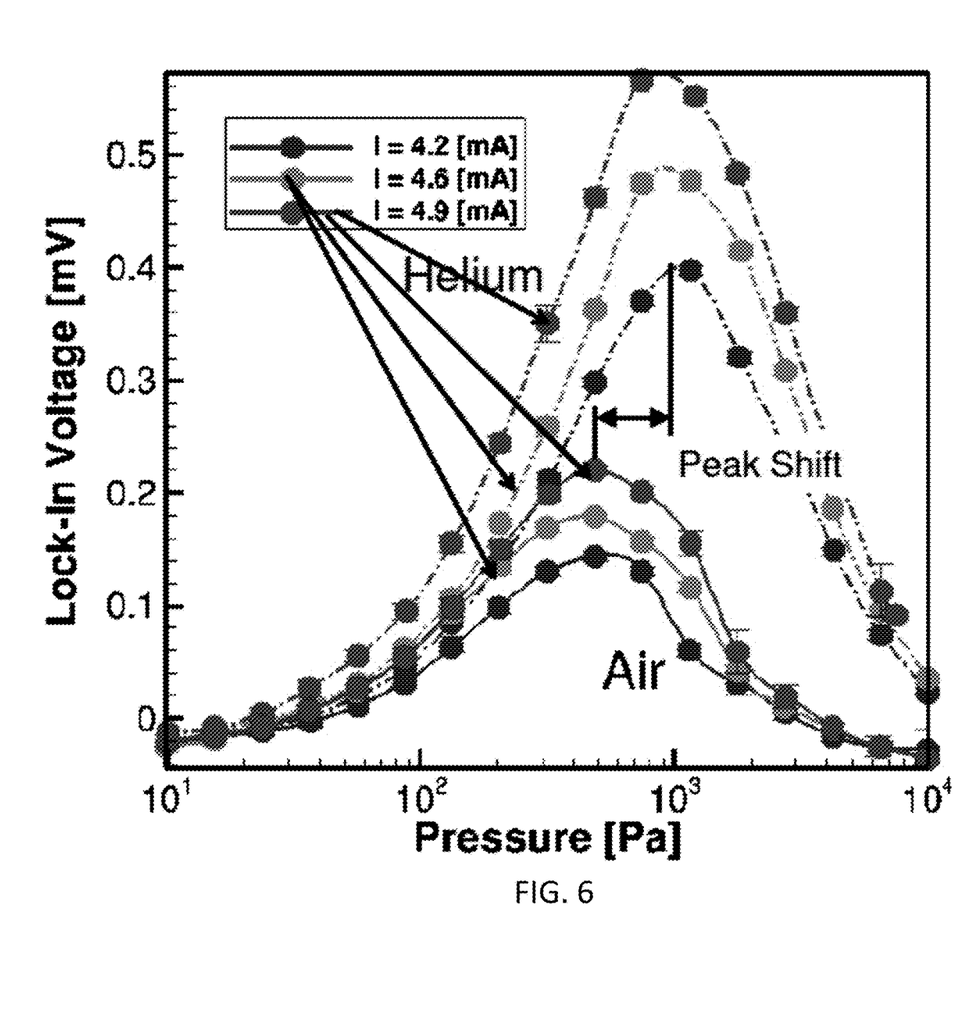
FIG. 6 are plots of pressure (in Pa) vs. lock-in voltages (in mV) measured at the sensing pads corresponding to different concentration of known constituents (in this case air and Helium) when combined with data associated with heat loss at the heating arms of the stationary assembly.

Referring to FIG. 6, plots of pressure (in Pa) vs. lock-in voltages (in mV) are provided for different current levels applied to the heating elements. Once combined with the measured resistance data of the heating elements (thereby establishing a correlation with heat transfer due to various concentrations of known constituents) concentration of known constituents (in this case air and Helium) can be ascertained.

Those skilled in the art will recognize that numerous modifications can be made to the specific implementations described above. The implementations should not be limited to the particular limitations described. Other implementations may be possible.

The invention claimed is:

1. A microelectromechanical (MEMS) gas sensor operating based on Knudsen thermal force, comprising:
   a substrate;
   at least one stationary assembly fixedly coupled to the substrate, the at least one stationary assembly terminating at corresponding pads configured to receive an electrical current for heating the at least one stationary assembly;
   at least one moveable assembly disposed above the substrate and biased to move substantially according to a main axis and juxtaposed with the at least one stationary assembly,
   the at least one moveable assembly configured to be selectively moveable along the main axis with respect to the at least one stationary assembly such that pressure applied to the at least one stationary assembly in the heated state and the at least one moveable assembly forms Knudsen forces applied to the at least one moveable assembly causing active movement of the at least one moveable assembly substantially along the main axis;
   the at least one stationary assembly comprising
   a base portion; and
   at least one heating arm extended outward from the base portion;
   the at least one moveable assembly comprising
   a base portion; and
   at least one sensing arm extended from the base portion, the at least one extended sensing arm juxtaposed with a corresponding heating arm;
   an actuation mechanism coupled to an actuation end of the at least one moveable assembly and configured to cause the selective movement; and
   a sensing mechanism coupled to a sensing end of the at least one moveable assembly opposite the actuation end, the sensing mechanism configured to sense the active movement of the at least one moveable assembly.

2. The MEMS gas sensor of claim 1,
   the actuation mechanism comprising an actuation capacitor coupled to actuation pads, such that applying a current to the actuation pads results in the selective movement of the moveable assembly due to electrostatic forces; and
   the sensing mechanism comprising a sensing capacitor coupled to sensing pads, such that the active movement of the moveable member results in changes in capacitance of the sensing capacitor.

3. A microelectromechanical (MEMS) gas sensor operating based on Knudsen thermal force, comprising:
   a substrate;
   at least one stationary assembly fixedly coupled to the substrate, the at least one stationary assembly terminating at corresponding pads configured to receive an electrical current for heating the at least one stationary assembly;
   at least one moveable assembly disposed above the substrate and biased to move substantially according to a main axis and juxtaposed with the at least one stationary assembly,
   the at least one moveable assembly configured to be selectively moveable with respect to the at least one stationary assembly such that at a known pressure applied to the at least one stationary assembly in the heated state and the at least one moveable assembly, movement of the at least one moveable assembly correlated to identity of concentration of known constituents of gases applying the known pressure;
   the at least one stationary assembly comprising
   a base portion; and
   at least one heating arm extended outward from the base portion;
   the at least one moveable assembly comprising
   a base portion; and
   at least one sensing arm extended from the base portion, the at least one extended sensing arm juxtaposed with a corresponding heating arm;
   an actuation mechanism coupled to an actuation end of the at least one moveable assembly and configured to cause the selective movement; and
   a sensing mechanism coupled to a sensing end of the at least one moveable assembly opposite the actuation end, the sensing mechanism configured to sense the active movement of the at least one moveable assembly.

4. The MEMS gas sensor of claim 3,
   the actuation mechanism comprising an actuation capacitor coupled to actuation pads, such that applying a current to the actuation pads results in the selective movement of the moveable assembly due to electrostatic forces; and
   the sensing mechanism comprising a sensing capacitor coupled to sensing pads, such that the active movement of the moveable member results in changes in capacitance of the sensing capacitor.

5. A system operating based on Knudsen thermal force, comprising:

a microelectromechanical (MEMS) gas sensor, comprising
a substrate,
at least one stationary assembly fixedly coupled to the substrate, the at least one stationary assembly terminating at corresponding pads configured to receive an electrical current for heating the at least one stationary assembly,
at least one moveable assembly disposed above the substrate and biased to move substantially according to a main axis and juxtaposed with the at least one stationary assembly,
the at least one moveable assembly configured to be selectively moveable along the main axis with respect to the at least one stationary assembly such that pressure applied to the at least one stationary assembly in the heated state and the at least one moveable assembly forms Knudsen forces applied to the at least one moveable assembly causing active movement of the at least one moveable assembly substantially along the main axis;
an actuation mechanism coupled to an actuation end of the at least one moveable assembly and configured to cause the selective movement; and
a sensing mechanism coupled to a sensing end of the at least one moveable assembly opposite the actuation end, the sensing mechanism configured to sense the active movement of the at least one moveable assembly.

6. The system of claim 5, the at least one stationary assembly comprising
a base portion; and
at least one heating arm extended outward from the base portion.

7. The system of claim 6, the at least one moveable assembly comprising
a base portion; and
at least one sensing arm extended from the base portion, the at least one extended sensing arm juxtaposed with a corresponding heating arm.

8. The system of claim 5,
the actuation mechanism comprising an actuation capacitor coupled to actuation pads, such that applying a current to the actuation pads results in the selective movement of the moveable assembly due to electrostatic forces; and
the sensing mechanism comprising a sensing capacitor coupled to sensing pads, such that the active movement of the moveable member results in changes in capacitance of the sensing capacitor.

* * * * *